United States Patent [19]

Shirasaki et al.

[11] Patent Number: 4,830,019
[45] Date of Patent: May 16, 1989

[54] ELECTRONIC BLOOD PRESSURE METER

[75] Inventors: Osamu Shirasaki, Amagasaki; Hiroshi Ogawa, Nagaoakakyo; Yoshinori Miyawaki, Yawata; Kazuhiro Matumoto, Kyoto, all of Japan

[73] Assignee: Omron Tateisi Electronics Co., Kyoto, Japan

[21] Appl. No.: 60,789

[22] Filed: Jun. 12, 1987

[30] Foreign Application Priority Data

Jun. 12, 1986 [JP] Japan .................................. 61-137908

[51] Int. Cl.⁴ .............................................. A61B 5/02
[52] U.S. Cl. ..................................... 128/681; 128/680
[58] Field of Search ................. 128/672, 677, 680-682

[56] References Cited

U.S. PATENT DOCUMENTS

| | | | |
|---|---|---|---|
| 4,030,484 | 6/1977 | Kuska et al. | 128/672 |
| 4,117,835 | 10/1978 | Williams | 128/677 |
| 4,307,727 | 12/1981 | Haynes | 128/672 |
| 4,461,266 | 7/1984 | Hood, Jr. et al. | 128/677 |
| 4,469,107 | 9/1984 | Asmar et al. | 128/681 |
| 4,597,393 | 7/1986 | Yamakoshi et al. | 128/677 |
| 4,699,152 | 10/1987 | Link | 128/677 |
| 4,703,760 | 11/1987 | Miyawaki et al. | 128/681 |

FOREIGN PATENT DOCUMENTS

| | | | |
|---|---|---|---|
| 154995 | 7/1985 | European Pat. Off. | 128/682 |
| 2092309 | 8/1982 | United Kingdom | 128/672 |

Primary Examiner—Lee S. Cohen
Assistant Examiner—David Shay
Attorney, Agent, or Firm—Wegner & Bretschneider

[57] ABSTRACT

An electronic blood pressure meter, equipped with the functions of computing at least a single relative pulse wave amplitude value in relation with a maximum pulse wave amplitude value, computing a blood pressure value from the cuff pressure when an amplitude of the pulse wave signal has coincided with the relative amplitude value during a change in the amplitude value of the pulse wave signal, and using the reference pressure value thus obtained in accordance with a certain arithmetic formula. If desired, a different process may be selected for determining a blood pressure depending on an initial cuff pressure. This electronic blood pressure allows a measurement to be completed in a very short time and minimizes the discomfort of the person whose blood pressure is to measured through reduction of the maximum cuff pressure. Yet the mathematical formula can be reduced to a simple arithmetic algorithm and is therefore easy to implement.

6 Claims, 12 Drawing Sheets

FIG. 4
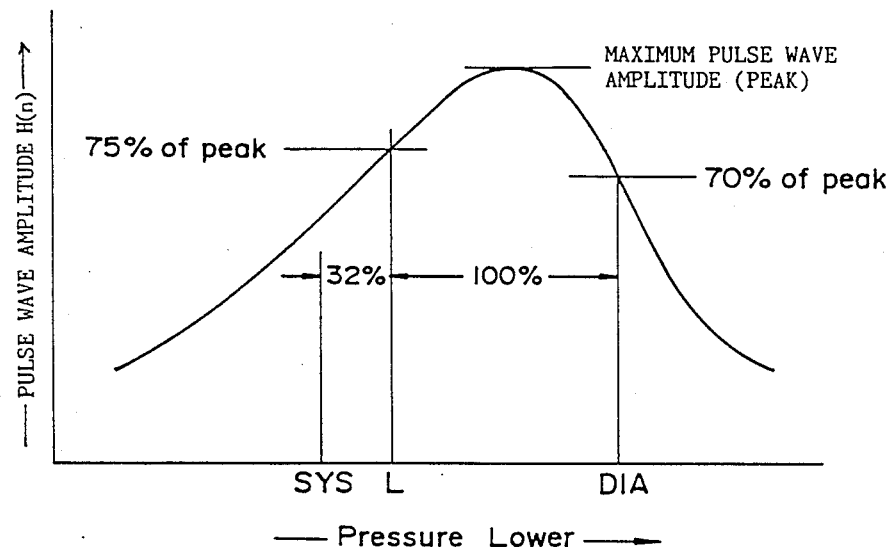
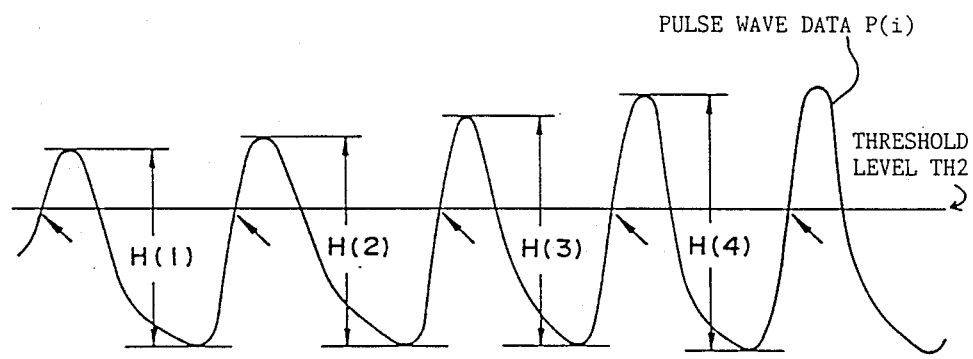
FIG. 5

FIG. 8
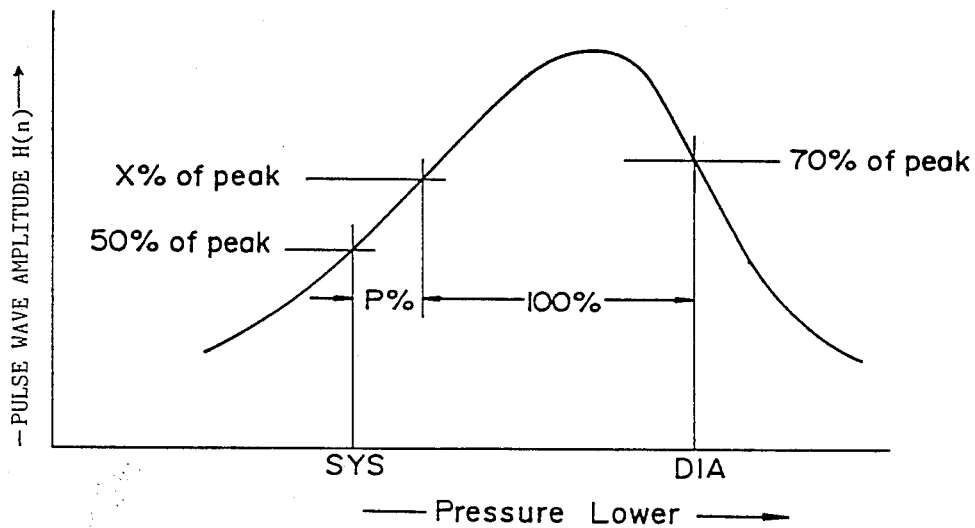
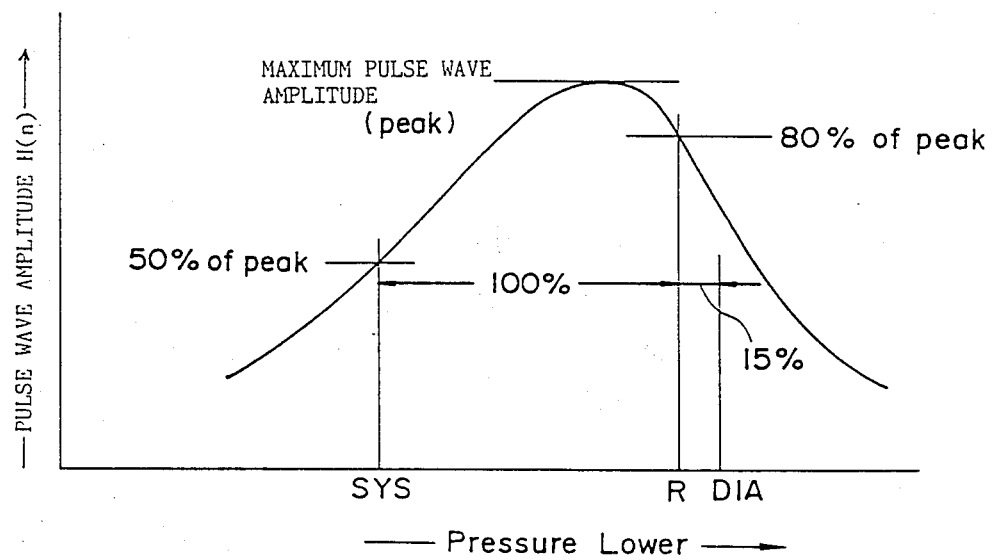
FIG. 12

ELECTRONIC BLOOD PRESSURE METER

TECHNICAL FIELD

The present invention relates to an electronic blood presure meter based on the oscillation method and in articular to an electronic blood pressure meter which can reduce the time required for measurement by reducing the cuff that is needed for blood pressure measurement.

BACKGROUND OF THE INVENTION

An electronic blood pressure meter based on the oscillation method comprises a cuff, a pressurization pump, a vent valve for depressurizing the cuff, a pressure sensor for detecting the cuff presure, and a micro computer (MPU).

This MPU is equipped with the functions of detecting a pulse wave component from the output signal of the pressure sensor, computing a pulse wave amplitude value from the pulse wave component and determining a systolic pressure (SYS) and a diastolic pressure (DIA) from the cuff pressure and the pulse wave amplitude value.

In this electronic blood pressure meter base on the oscillation method, a threshold value is utilized as a basis for determining the blood pressure values.

Normally, in measuring blood pressure, with an artery blocked by pressurizing the cuff, a pulse wave amplitude is detected during the course of gradually depressurizing the cuff. The pulse wave is an indication of a deformation of the artery wall and the surround tissue due to the pulsation in the internal pressure of the artery, and this is transmitted to the cuff where it is detected as a pressure fluctuation. This pulse wave amplitude value gradually increases as the cuff pressure is reduced and can be represented by a curve (envelope) which gradually increases but after reaching a maximum value diminishes in value.

Thus, a maximum pulse wave amplitude value is detected and a pulse wave amplitude value which is substantially equal to a threshold value which is a certain fraction of the maximum pulse wave amplitude value (for instance 50% of the maximum pulse wave amplitude value) is determined during the gradually increasing process of the pulse wave amplitude value. And the blood pressure when the pulse wave amplitude value has substantially coincided with the threshold value is determined as a systolic pressure. Likewise a pulse wave amplitude value which is substantially equal to another threshold value which is also a certain fraction of the maximum pulse wave amplitude value (for instance 70% of the maximum pulse wave amplitude value) is determined during the gradually decreasing process of the pulse wave amplitude value, and the blood pressure when the pulse wave amplitude value has substantially coincided with the threshold value is determined as a diastolic pressure.

In such a conventional electronic blood pressure meter based on the oscillation method, the cuff pressure corresponding to the time point when the pulse wave amplitude value is 50% of the maximum pulse wave amplitude value is determined as a systolic pressure and the cuff pressure corresponding to the time point when the pulse wave amplitude value is 70% of the maximum pulse wave amplitude value is determined as a diastolic pressure.

According to this process, it is necessary to detect the pulse wave amplitude value corresponding to 50% of the maximum pulse wave amplitude value for the purpose of determining the systolic pressure. Therefore, the cuff pressure must be raised beyond the systolic pressure at which the pulse wave amplitude value corresponds to 50% of the maximum pulse wave amplitude value. Thus, not only a considerable time is required for measurement but also congestion could be cause in blood vessels which are more periheral than the part of the artery to which the cuff is applied.

Further, because of the need to raise the cuff pressure beyond the systolic pressure, it can often happen that the cuff presurization is insufficient. In such case, the cuff pressure at the time point when the pulse wave amplitude corresponds to 50% of the maximum pulse wave amplitude value cannot be detected and the measurement has to be repeated all over again. Furthermore, because it becomes known to the person using the blood pressure meter that the cuff pressure was insufficient only after the attempt to measure blood pressure has been concluded, the patient must endure the discomfort caused by the excessive cuff pressure for an unreasonably long time.

BRIEF SUMMARY OF THE INVENTION

In view of such problems of the prior art, a primary object of the present invention is to provide an electronic blood pressure meter which is free from the problems of the prior art and allows a measurement to be completed in a very short time.

Another object of the present invention is to provide an electronic blood pressure meter which minimizes the discomfort of the person whose blood pressure is to measure through reduction of the maximum cuff pressure.

Yet another object of the present invention is to provide an electrnic blood pressure meter which is based on a simple arithmetic algorithm and is therefore easy to implement.

In order to achieve this object, the electronic blood pressure meter of the present invention comprises a cuff, a pressurization means for pressurizing the cuff, a pressure detection means for detecting a fluid pressure inside the cuff, a pulse wave detection means for detecting a pulse wave component contained in an output signal of the pressure detection means, a pulse wave amplitude value computing means for computing a pulse wave amplitude value from the pulse wave component detected by the pulse wave component detecting means, and a blood pressure determining means for determining a systolic pressure and a diastolic pressure from an output signal of the pulse wave amplitude computing means, a relative amplitude value computing means for computing at least a single relative pulse wave amplitude value in relation with a maximum pulse wave amplitude value obtained by the pulse wave amplitude value computing means, a reference pressure value computing means for computing a blood pressure value from the cuff pressure when an amplitude of the pulse wave signal has coincided with the relative amplitude valve during a change in the amplitude value of the pulse wave signal, and a blood pressure computing means for comuting a blood pressure value using the reference pressure value obtained by the reference pressure value computing means in accordance with a certain arithmetic formula.

According to the electronic blood pressure meter of this structure, after the pulse wave amplitude value has been detected and the maximum pulse wave amplitude value has been detected, the cuff pressure at the time when the pulse wave amplitude value corresponds to, for instance, 70% of the maximum pulse wave amplitude value during the decreasing process of the pulse wave amplitude is determined as a diastolic pressure (DIA). Then, the cuff pressure (L value) at the time when the pulse wave amplitude value corresponds to 75% of the maximum pulse wave amplitude value during the increasing process of the pulse wave amplitude value is determined. Then, 32% of the difference between the L value of DIA is added to the L value and this sum is determined as a systolic pressure (SYS).

Therefore, according to this systolic pressure determining means, a systolic pressure can be computed by finding a pulse wave amplitude value which corresponds to 75% of the maximum pulse wave amplitude value. Because the cuff pressure at the time point when the pulse wave amplitude value is 75% of the maximum pulse wave amplitude value is lower than the cuff pressure at the time poin when the pulse wave amplitude value is 50% of the maximum pulse wave amplitude value, the pressure requirement for the present invention is substantially lower than the prior art electronic blood pressure meters. Therefore, not only because of the time required for measurement is reduced but also because the possibility of improper measurement due to insufficient cuff pressurization can be reduce, the possibility of causing congestion in the person whose blood pressure is to be measured can be significantly reduced.

Whereas a conventional electronic blood pressure meters is incapable of any blood pressure measurement if the initial cuff pressurization was insufficient, the electronic blood pressure meter of the present invention is capable of blood presure measuremenet even when the cuff pressure is insufficient by using an appropriate algorithm for computing the systolic pressure.

Thus, since it is not necessary to pressurizing the cuff beyond the systolic pressure of the patient any more, there will be no need for excessively pressurizing the cuff and the time required for blood pressure measurement will be significantly reduced.

According to a certain aspect of the present invention, the reference pressure value used in the step of computing the systolic pressure includes the diastolic pressure obtained during a same measurement process according to an arbitrary but different method and a second reference blood pressure which is different from the former, the systolic pressure being determined by adding a fraction of a pressure difference between the diastolic pressure and the second reference blood pressure to either one of the diastolic pressure and the second reference blood pressure.

According to another aspect of the present invention, the reference pressure vaue used in the step of computing the diastolic pressure includes the systolic pressure obtained during a same measurement process according to an arbitrary but different method and a second reference blood pressure which is different from the former, the diastolic pressure being determined by subtracting a fraction of a pressure difference between the systolic pressure and the second reference blood pressure to either one of the systolic pressure and the second reference blood pressure.

According to yet another aspect of the present invention, the relative amplitude value which is used in the process of obtaining the systolic pressure is a pulse wave amplitude value at an arbitrary cuff pressure which is higher than a cuff pressure at which the maximum pulse wave amplitude is detected, and a ratio of the pulse wave amplitude value at the arbitrary cuff pressure to the maximum pulse wave amplitude value is used in the process of computing the diastolic pressure.

According to yet another aspect of the present invention, the relative amplitude value which is used in the process of obtaining the systolic pressure is a pulse wave amplitude value at an arbitrary cuff pressure which is lower than a cuff pressure at which the maximum pulse wave amplitude is detected, and a ratio of the pulse wave amplitude value at the arbitrary cuff pressure to the maximum pulse wave amplitude value is used in the process of computing the diastolic pressure.

According to yet another aspect of the present invention, a different process is selected for determining a blood pressure depending on an initial cuff pressure.

BRIEF DESCRIPTION OF THE DRAWINGS

The present invention will now be shown and described in the following in terms of concrete embodiments thereof with reference to the appended drawings, in which:

FIG. 4 is a graph for illustratingthe process of determining the blood pressures in the electronic blood pressure meter of the first embodiment;

FIG. 5 is a graph for illustrating the breaks in the pulse wave data;

FIG. 8 is a graph for illustrating the process of determining the blood pressures in the electronic blood pressure meter of the third embodiment;

FIG. 12 is a graph for illustrating the process of determining the blood pressures in the electronic blood pressure meter of the fourth embodiment.

DETAILED DESCRIPTION OF THE PREFERRED EMBODIMENTS

Figure 1:
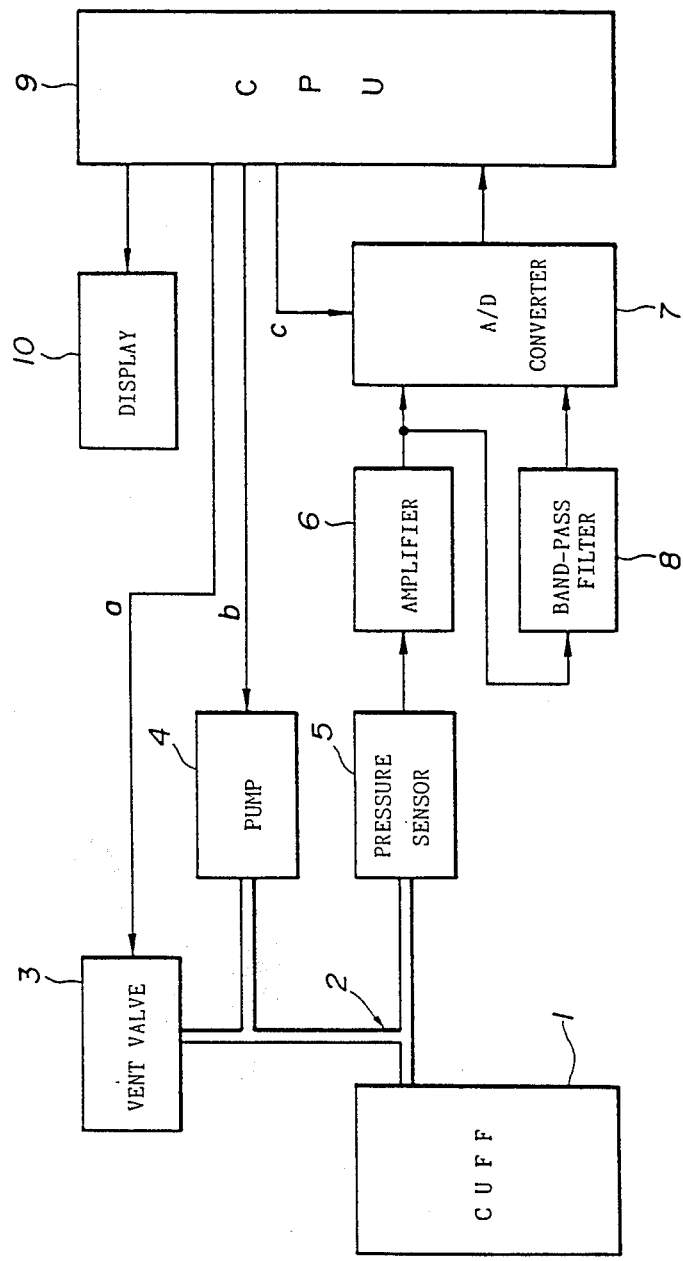
FIG. 1 is a block diagram showing the circuit structure of an embodiment of the electronic blood pressure meter of the present invention.

FIG. 1 shows a block diagram of a concrete embodiment of the pneumatic system and the measurement circuit of the electronic blood pressure meter according to the present invention. In this embodiment of the present invention a cuff 1 is connected to a pressurization pump (pressurizing means) 4, a vent valve (venting means) 3 and a pressure sensor (pressure detecting means) 5, by way of a tube 2. The vent valve 3 includes a pair of valves consisting of a rapid vent valve and a gradual vent valve. The pressure sensor 5 may consist of any pressure transducer which can covert pressure into an electric signal such as a diaphragm pressure converter using a strain gauge and a semiconductor pressure converter element. The pressurization pump 4 and the vent valve 3 are controlled by a CPU (central processing unit) 9 which is described hereinafter.

The output (analog) signal of the pressure sensor 5 is amplified by an amplifier 6 and is then converted into a digital signal by an A/D converter 7. The CPU receives the output signal of the pressure sensor 5 converted into a digital signal by the A/D converter 7 at a certain frequency. The output signal of the pressure sensor 5 is also sent to a band pass filter 8, by way of the amplifier 6, in which a pulse wave component is extracted from the cuff pressure signal, and the extracted pulse wave signal (pulse wave component) is supplied to the CPU 9. The CPU 9 is additionally provided with the functions of computing a pulse wave amplitude value, computing a relative amplitude value from the pulse wave amplitude value, computing a reference pressure value from the relative amplitude value and computing a systolic and a diastolic pressure from the reference pressure value. Further, the CPU 9 is connected to a display unit 10 for displaying a systolic and a diastolic pressure value.

FIG. 4 is a graph for illustrating the computing process according to which the electronic blood pressure meter of this embodiment determines a blood pressure value from a pulse wave envelope.

A pulse wave envelope is normally obtained in the form as shown in FIG. 4. In a conventional electronic blood pressure meter, a systolic pressure (SYS) and a diastolic pressure (DIA) were determined as the cuff pressures corresponding to the time points when the pulse wave amplitude corresponds to 50% and 70% of the maximum pulse wave amplitude value before and after the occurrence of the maximum pulse wave amplitude value (peak value), respectively, as mentioned earlier. On the other hand, a primary feature of the present embodiment exists in finding a cuff pressure value L (mmHg) at the time point when the pulse wave amplitude value corresponds to 75% of the maximum pulse wave amplitude before the occurrence of the maximum pulse wave amplitude value instead of finding the pulse wave amplitude value (SYS) corresponding to 50% of the maximum pulse wave amplitude value. Note that the pressure value L is substantially lower than the systolic pressure or the cuff pressure at the time point when the pulse wave amplitude value corresponds to 50% of the maximum pulse wave amplitude.

Then, the diastolic pressure (DIA) is determined as the cuff pressure at the time point when the pulse wave amplitude value corresponds to 70% of the maximum pulse wave amplitude value in a conventional manner when the pulse wave amplitude value is decreasing with decreasing cuff pressure. And the systolic pressure is computed as follows:

$$SYS = L + 0.32(L - DIA) \text{ (mmHg)}$$

In other words, the systolic pressure (SYS) is computed by using the cuff pressure L at the time when the pulse wave amplitude corresponds to 75% of the maximum pulse wave amplitude value as a reference value, adding 32% of the difference between the L value and DIA to the L value and determining this sum as a systolic pressure.

Figure 2A:
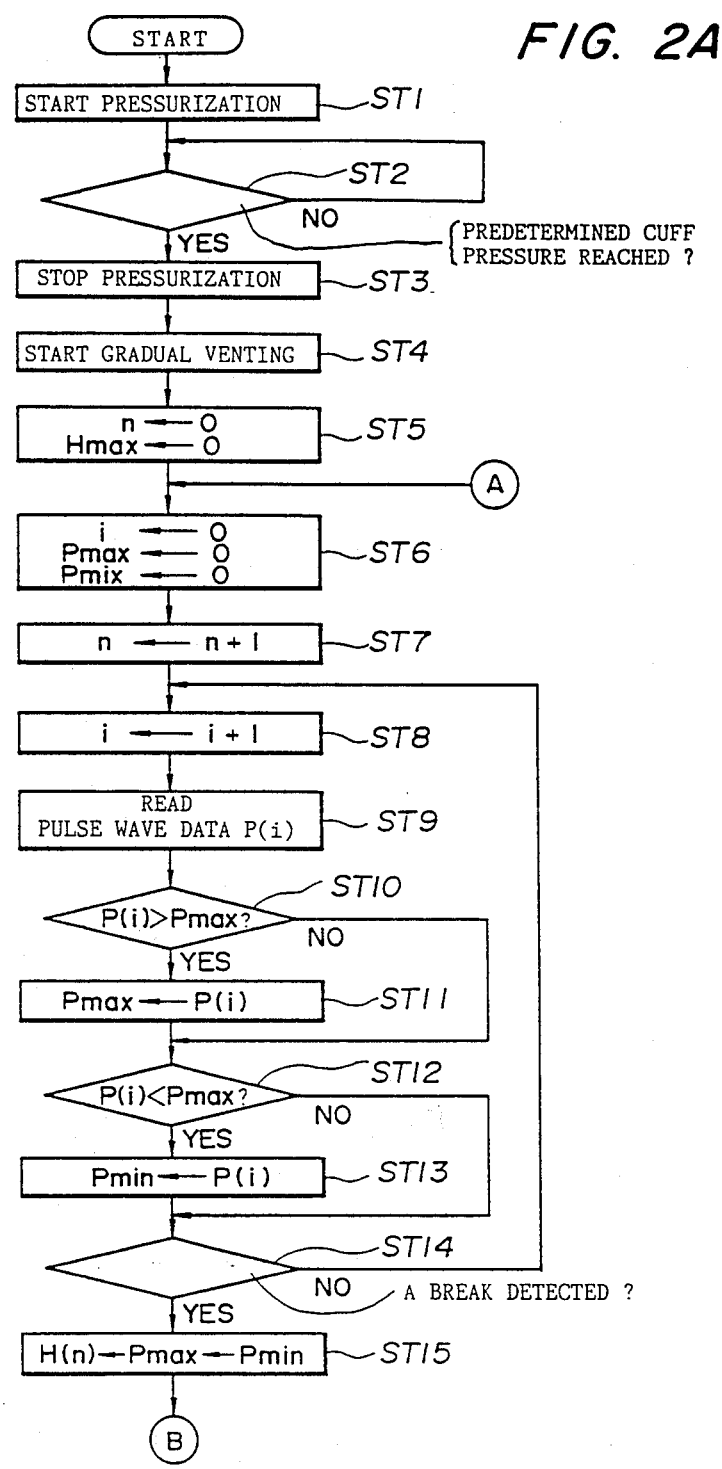
FIGS. 2a and 2b constitute a flow chart showing the processing action of an embodiment of the electronic blood pressure meter of the present invention.
Figure 2B:
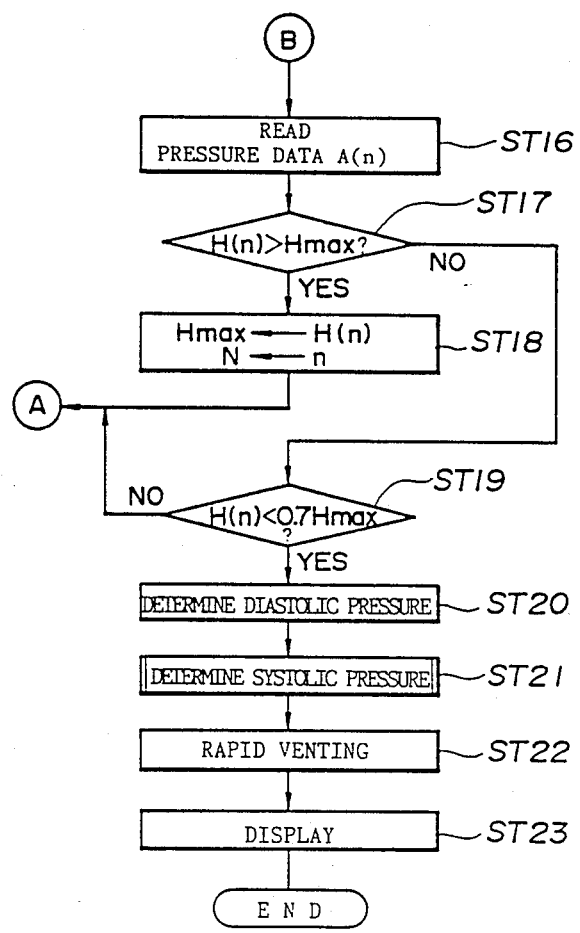

FIGS. 2a and 2b constitute a flow chart showing the actual processing action of the electronic blood pressure meter of the first embodiment.

When the action of the electronic blood pressure meter of the present embodiment is initiated, the pressurization pump 4 is activated by a signal b (refer to FIG. 1) from the CPU 9 and the cuff 1 is pressurized (ST1 or step 1). When the cuff pressure has been increased to a predetermined pressure level, it is detected by the CPU 9 (ST2) and the pressurization process is completed by stopping the action of the pressurization pump 4 (ST3). Thereafter, the vent valve 3 begins a gradual venting action (ST4) controlled by a control signal a from the CPU 9 according to a certain program stored in the permanent memory incorporated in the CPU 9 and the system flow advances to the succeeding stage of determining blood pressure values which is described hereinafter.

First of all, variables n and Hmax are cleared in an initializing step (ST5). The variable n is a count of the pulse wave which is incremmented by the CPU 9 for each pulsation of the pulse wave while the variable Hmax is a hold value of the current maximum pulse wave amplitude value for detecting the ultimate maximum pulse wave amplitude value.

Then, variables i, Pmax and Pmin are cleared in another initialization step (ST6). The variable i is an index value of the cuff pressure data A(i) and the pulse wave data P(i) which are inputted to the CPU 9 from the A/D converter 7 while the variables Pmax and Pmin retain the maximum and minimum pulse wave amplitude values for computing the pulse wave amplitude value for each pulsation of the pulse wave.

Thereafter, after the variable n is incremented (ST7) and the variable i is likewise incremented (ST8), the pulse wave data P(i) is transmitted from the A/D converter 7 to the CPU 9 according to a control signal c given to the A/D converter 7 from the CPU 9 (ST9). The value of the pulse wave data P(i) is then compared with Pmax (ST10) and, if P(i) is greater than Pmax, Pmax is updated by replacing the value of Pmax with that of P(i) in ST11. Then, the system flow advances to ST12. Otherwise or if P(i) is not greater than Pmax, the system flow advances directly from ST10 to ST12.

In ST12, the value of P(i) is compared with Pmin and if P(i) is smaller than Pmin the value of P(i) is substituted into Pmin for purpose of updating Pmin (ST13) before the system flow advances to ST14. Otherwise, the system flow advances directly from ST12 to ST14.

In ST14 it is determined whether a break in the pulse wave data has been detected or not. A break of the pulse wave data is defined as a point of intersection between the pulse wave data P(i) with a certain threshold level TH2 as the pulse wave amplitude increases as indicated by each of the arrows shown in FIG. 5 and gives a dividing point in the pulse wave signal for each pulsation thereof.

When a break in the pulse wave has been detected, the system flow advances to ST15 but if it is not detected the process of ST8 through ST14 is repeated on the succeeding pulse wave data. Suppose that a break in the pulse wave data has been detected. Then, the difference between Pmax and Pmin is computed and this difference is substituted into the pulse wave amplitude value H(n) (ST15).

The cuff pressure data is obtained from the A/D converter 7 and the cuff pressure value A(n) corresponding to the pulse wave amplitude value H(n) is supplied to the CPU 9 (ST16).

In ST17, it is determined whether H(n) is greater than Hmax or not. If H(n) is greater than Hmax, then, the determination result of ST 17 is affirmative and Hmax is updated by substituting the value of H(n) into Hmax and the count n if the pulse wave counter is substituted into the variable N to be retained therein (ST18). Thereafter, the system flow returns to ST6 and the process in ST6 through ST18 is repeated. If the pulse wave amplitude value has not reached the maximum value and is still increasing, H(n) is always greater than Hmax and this updating process is repeated until the maximum value of the pulse wave amplitude value has been reached.

Suppose that H(n) has become smaller than Hmax. Then, the determination result of ST17 is negative and the system flow advances to ST19. In ST19, it is determined whether the pulse wave amplitude value H(n) is smaller than 0.7 Hmax or not. In other words, it is determined whether the pulse wave amplitude value has reached the level of 70% of the maximum value while the pulse wave amplitude value is decreasing after reaching the maximum value nor not. Here, when the pulse wave amplitude value corresponds to 70% of the maximum pulse wave amplitude value the cuff pressure represents the diastolic pressure.

Suppose that the pulse wave amplitude value H(n) is greater than 70% of the maximum pulse wave amplitude value Hmax. Then, the determinatiion result of ST19 is negative. Therefore, the system flow returns to ST6 and the process in ST7 through ST19 is repeated. Suppose that the pulse wave amplitude value has reached 70% of the maximum pulse wave amplitude value. Then, the determination result of ST19 is affirmative and the cuff pressure A(n) at that moment is determined to be the diastolic pressure (DIA) (ST20). Thereafter, the systolic pressure is determined in ST21 through the process which is described hereinafter and the measurement is completed after rapidly venting the cuff (ST22) and displaying the systolic and diastolic pressure value on the display unit 10 (ST23).

Figure 3:
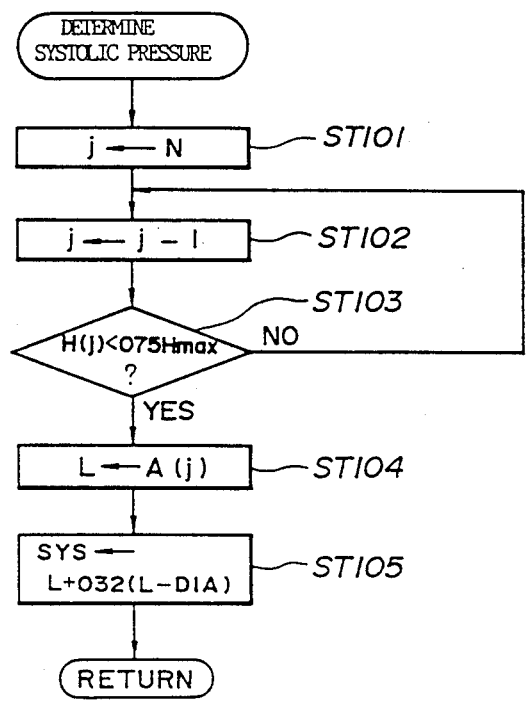
FIG. 3 is a flow chart showing an essential part of the processing action of the systolic pressure in the first embodiment.

FIG. 3 is a flow chart of the subroutine for actually determining the systolic pressure in ST21.

First of all, the number N of the maximum pulse wave amplitude value is substituted into the variable j (ST101) and the variable j is decremented (ST102). In succeeding ST103, it is determined whether the pulse wave amplitude value H(j) is smaller than 0.75 Hmax or not. In other words, the cuff pressure L (at the time point when the pulse wave amplitude value corresponding to 75% of the maximum pulse wave amplitude value) which serves as a reference value for determining the systolic pressure as shown in FIG. 4 is now going to be obtained.

If the pulse wave amplitude value H(j) is greater than 75% of the maximum pulse wave amplitude value, the determination result of ST103 is negative and the system flow returns to ST102. In other words, as long as the pulse wave amplitude value H(j) indexed by the variable j is not smaller than 0.75 Hmax, the process in ST102 and ST103 is repeated.

Suppose that the pulse wave amplitude value H(j) has become smaller than 75% of the maximum pulse wave amplitude value, then, the determination result of ST103 is affirmative and the cuff pressure A(j) when the H(j) has fallen below the critical value is set as the pressure value L (ST104).

Then, the systolic pressure value is computed according to the following formula (ST105) and the system flow returns from the subroutine for computing the systolic pressure to the main flow.

$$SYS = L + 0.32(L - DIA)$$

In the above described embodiment, the systolic pressure (SYS) was derived by finding the cuff pressure value L at the time point when the pulse wave amplitude value corresponds to 75% of the maximum pulse wave amplitude value. But, according to the broadest concept of the present invention, it is also possible to derive the systolic pressure normally from the cuff pressure at the time point when the pulse wave amplitude corresponds to 50% of the maximum pulse wave amplitude value but use the cuff pressure at the time point when the pulse wave amplitude value corresponds to 75% of the maximum pulse wave amplitude value for deriving the systolic pressure only when the initial cuff pressure was so low that the pulse wave amplitude value corresponding to 50% of the maximum pulse wave amplitude value pressure was not detected.

Figure 6:
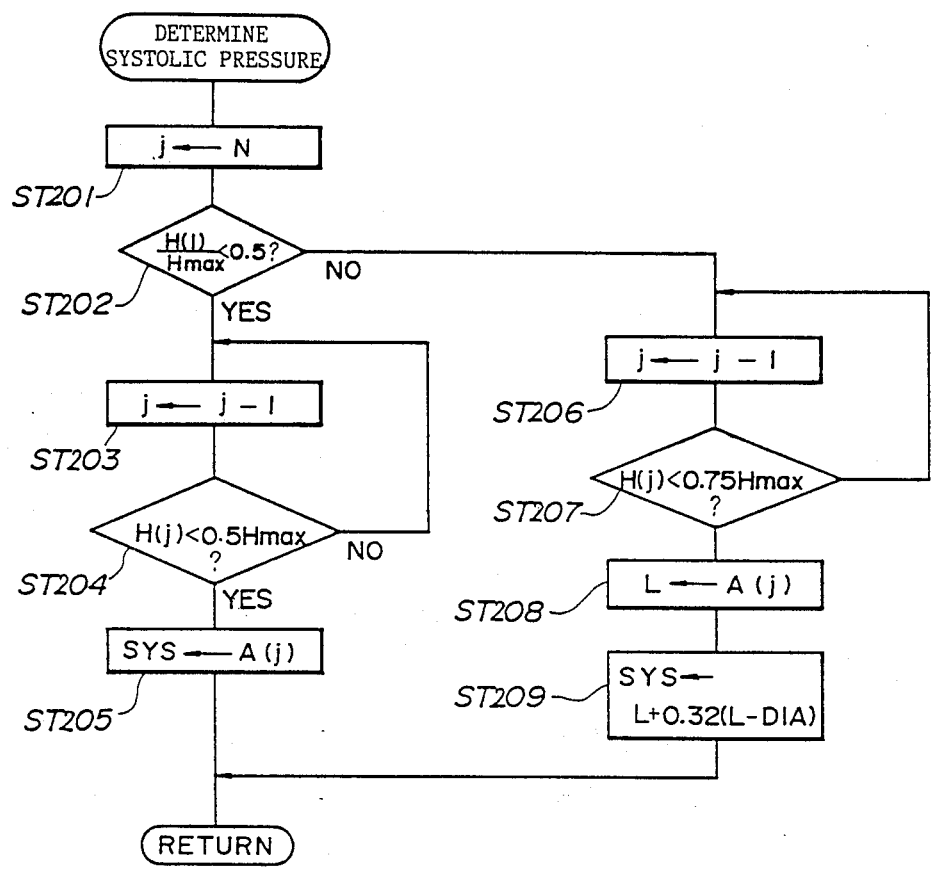
FIG. 6 is a flow chart showing an essential part of the processing action of the systolic pressure in the first embodiment according to the second embodiment of the present invention.

FIG. 6 shows an alternative subroutine for determining the systolic pressure in accordance with a second embodiment of the present invention which is different from the first embodiment in the way ST21 is carried out. This embodiment is characterized by the process of determining the systolic pressure, and the diastolic pressure may be determined in the same manner as in the first embodiment.

In this embodiment, the systolic pressure is computed from the cuff pressure at the time point when the pulse wave amplitude corresponds to 75% of the maximum pulse wave amplitude value in accordance with the above mentioned formula only when the pulse wave amplitude corresponding to 50% of the maximum pulse wave amplitude was not detected, for instance, due to insufficient initial pressurization of the cuff. Otherwise, the cuff pressure at the time point when the pulse wave amplitude corresponds to 50% of the maximum pulse wave amplitude value is directly determined to be the systolic pressure.

First of all, the number N of the maximum pulse wave amplitude value is substituted into the variable j (ST201). Then, in ST202, it is determined whether the ratio H(1)/Hmax is less than 0.5 or not. If the ratio is less than 0.5, the system flow advances to the process of ST203 through ST205 and the systolic pressure is determined from the cuff pressure at which the pulse wave amplitude value H(j) corresponds to 50% of the maximum pulse wave amplitude value Hmax. If the ratio H(1)/Hmax is equal to or greater than 0.5 in ST202, the process in ST206 through ST209 is carried out and after the pressure value L (the cuff pressure at which the pulse wave amplitude value corresponds to 75% of the maximum pulse wave amplitude value) is determined the systolic pressure is computed from this pressure value L in accordance with the above mentioned formula.

When the system flow advances from ST202 to ST203, the variable j is decremented (ST203) and it is then determined whether the pulse wave amplitude H(j) specified by the variable j is less than 0.5 Hmax (ST204) or not. If H(j) is not less than 0.5 Hmax, the determination result of ST204 is negative and the system flow returns to ST203. Thus, the process of ST203 and ST204 is repeated until the value of H(j) specified by the variable j becomes less than 0.5 Hmax. Suppose that the pulse wave amplitude value H(j) has become less than 0.5 Hmax. Then, since the determination result of ST204 is affirmative, the current cuff pressure A(j) specified by the variable j is determined to be the systolic pressure (SYS) (ST205) and the system flow returns to the main flow from this subroutine for determining the systolic pressure.

Meanwhile, when the system flow advances from ST202 to ST206, the variable j is decremented (ST206) and it is determined whether the pulse wave amplitude value H(j) is less than 0.75 Hmax or not (ST207). When H(j) is not less than 0.75 Hmax, the system flow returns to ST206 and the process in ST206 and ST207 is repeated until H(j) gets less than 0.75 Hmax. When the H(j) has become less than 0.75 Hmax, the determination result of ST207 is affirmative and the cuff pressure A(j) which is specified by the variable j is set as the pressure value L (ST208). Thus, the systolic pressure is computed from the following equation (ST209) and the system flow returns to the main flow from this subroutine for determining the systolic pressure.

$$SYS = L + 0.32(L - DIA)$$

FIG. 8 illustrates the process of computing blood pressure values according to the third embodiment of the present invention. In this graph, P (%) denotes the ratio of the pressure difference between a pressure value M and the systolic pressure SYS to the pressure difference between the pressure value M and the diastolic pressure DIA, the pressure value M being the cuff pressure at the same point when the pulse wave amplitude value corresponds to X% of the maximum pulse wave amplitude value. And Table 1 given below shows the relationship between X(%) and P(%) which was obtained from a statistical study made on 225 persons.

TABLE 1

| X (%) | P (%) |
|---|---|
| 80.0 | 44.31 |
| 75.0 | 33.42 |
| 70.0 | 22.17 |
| 65.0 | 15.95 |
| 60.0 | 10.33 |
| 55.0 | 4.96 |
| 50.0 | 0.00 |

In the first embodiment the pulse wave amplitude value (L) corresponding to 75% of the maximum pulse wave amplitude value was used as a reference value in computing a systolic pressure, but in the present embodiment, as shown in FIG. 8, the pulse wave amplitude value corresponding to X% of the maximum pulse wave amplitude value is first determined in order to find the difference between the cuff pressure M at the time point when this X% pulse wave amplitude value was detected and DIA which may be derived in any conventional method, and the systolic pressure is determined as a sum of P% of this difference and the cuff pressure M corresponding to the X% pulse wave amplitude value.

In other words, in the present embodiment, it is evaluated when a first pulse wave amplitude value which may vary depending on the degree of the initial cuff pressure has occurred in relation with the occurrence of the maximum pulse wave amplitude value and the determination of SYS is based on a selection process in which if the first pulse wave amplitude value (X% pulse wave amplitude value) is less than 50% of the maximum pulse wave amplitude value, then, SYS is determined in the same way as in the conventional process and if the first pulse wave amplitude value is greater than 50%, then, SYS is determined according to a process which is described hereinafter.

Since the cuff pressure when the ratio of the pulse wave amplitude value to the maximum value is X(%) is M and the ratio of the pressure difference between M and the systolic pressure SYS to the pressure difference between M and the diastolic pressure DIA is P(%) by definition, the systolic pressure SYS can be expressed as follows:

$$SYS = M + (P/100)(M - DIA) \text{ (mmHg)}$$

Figure 9:
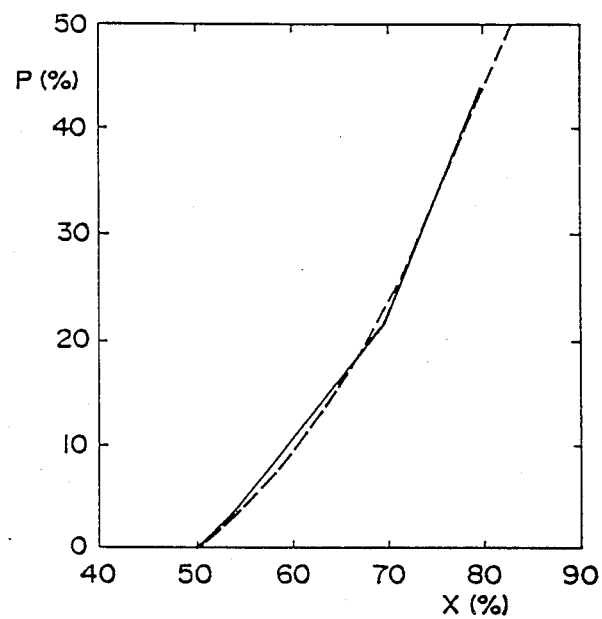
FIG. 9 is a graph showing the relationship between X and P.

In this embodiment, the relationship between P and X is found with a statistical technique and is introduced into the process of computing the systolic pressure. Table 1 shows the results obtained from the statistical data of the relationship between P and X of 225 samples. FIG. 9 shows this P-X relationship in the form of a graph. In this graph, the statistically obtained P-X curve is shown by the solid line while the broken line is an approximation of this curve which can be expressed by the following formula:

$$P = (x - 36)^2/40 - 5$$

Figure 7:
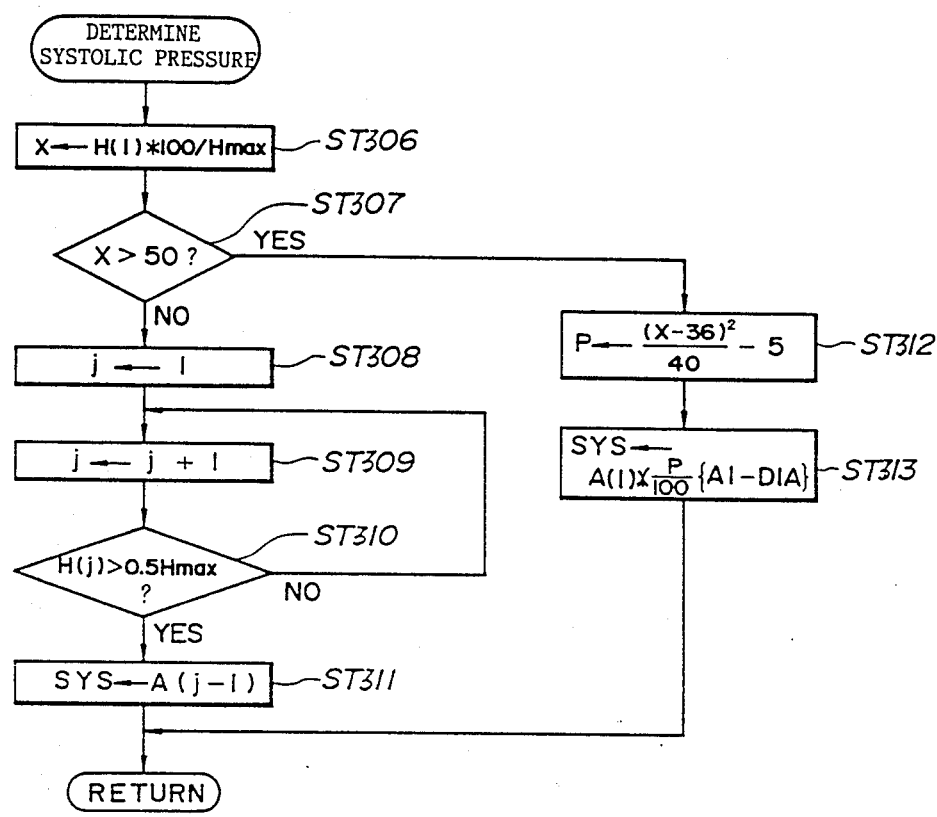
FIG. 7 is a flow chart showing an essential part of the processing action for determining the systolic pressure in accordance withh the third embodiment of the present invention.

FIG. 7 shows another alternative subroutine for determining the systolic pressure in accordance with a third embodiment of the present invention which is different from the previous embodiments in the way ST21 is carried out. And the working principle of this embodiment was described above with reference to FIGS. 8 and 9. This embodiment is characterized by the process of determining the systolic pressure, and the diastolic pressure may be determined in the same manner as in the first embodiment.

First of all, the means for determining the systolic pressure (which may be implemented by the functions of the CPU 9) in this embodiment detects what fraction X(%) of the maximum pulse wave amplitude value the first detected pulse wave amplitude value H(1) corresponds to, immediately after the start of blood pressure measurement. This fraction X% is computed with the following formula (ST306).

$$X = H(1) \cdot 100/Hmax$$

This fraction X(%) is the ratio of the first pulse wave amplitude value H(1) to the maximum pulse wave amplitude value Hmax. In succeeding ST307, it is determined whether X is greater than 50% or not. In this embodiment, the method for determining the systolic pressure is selected depending on whether the first detected pulse wave amplitude value is less than 50% of the maximum pulse wave amplitude value or not.

Suppose that the cuff pressurization was sufficient and a weak pulse wave was obtained from the beginning, or, in other words, that the value of H(1) is equal to or less than 50% of the maximum pulse wave amplitude. Then, the system flow advances to ST308 where the initial value of 1 is substituted into the pointer j, and j is incremented by 1 (ST309). Then, the pulse wave amplitude value H(j) specified by the value of j is compared with 50% of the maximum pulse wave amplitude value (ST310). If H(j) is greater than 0.5 Hmax the determination result in ST310 is affirmative and the cuff pressure value A(j−1) preceding the current cuff pressure specified by the pointer j is determined to be the systolic pressure (ST311). In other words, when the pulse wave amplitude value H(j) is less than 50% of the maximum pulse wave amplitude value, the systolic pressure is determined in the same way as in the conventional method. On the other hand, if the pulse wave amplitude value H(1) is found to be greater than 50% of the maximum pulse wave amplitude value, the determination result oof ST307 is negative and the system flow advances to ST312.

In ST312, P is computed with the following formula:

$$P = (X-36)^2/40 - 5$$

and the systolic pressure is computed as given by the following formula:

$$SYS = A(1) + [P/100][A(1) - DIA]$$

FIG. 12 illustrates the principle of yet another embodiment (a fourth embodiment) of the process of determining blood pressure according to the present invention.

In the previous embodiments, blood pressure was determined during the course of gradually reducing the cuff pressure after the cuff has been fully pressurized, but in the present embodiment blood pressure measurement takes place during the course of gradually pressurizing the cuff.

In the present embodiment, the systolic pressure may be determined according to a conventional process (the cuff pressure at the time when the pulse wave amplitude is 50% of the maximum value can be determined as the systolic pressure). And the pulse wave amplitude corresponding to 80% of the maximum pulse wave amplitude value as the pulse wave amplitude value decreases with decreasing cuff pressure is determined and the cuff pressure (R) at that time is used as a reference value foir determining the diastolic pressure. In other words, the difference between SYS and R is computed and the difference between R and 15% of the former difference value is determined as DIA.

Thus, the diastolic pressure is computed by the following formula:

$$DIA = R - 0.15(SYS - R)(mmHg)$$

In this embodiment, since the blood pressure values are obtained during the course of pressurizing the cuff, excessive pressurization of the cuff is avoided to an even greater extent and the time required for blood pressure measurement can be drastically reduced.

Figure 10A:
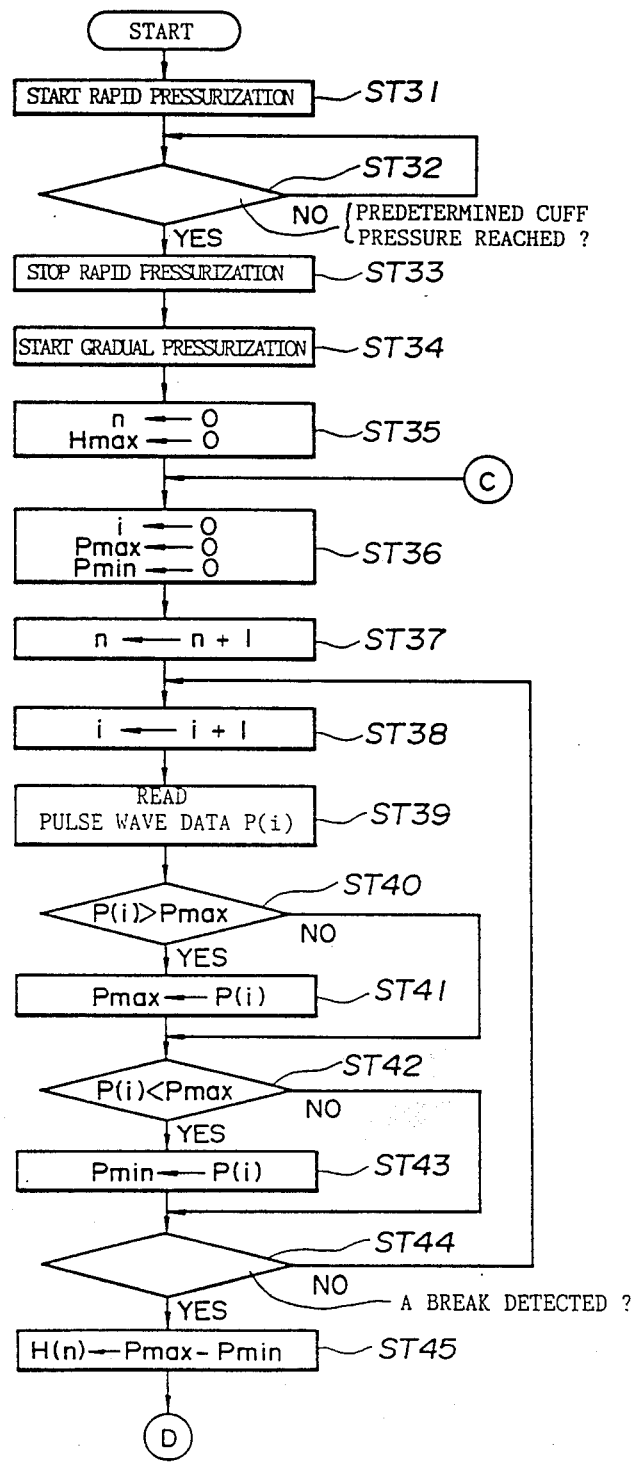
FIGS. 10a and 10b constitute a flow chart showing the processing actions of yet another (a fourth) embodiment of the present invention.
Figure 10B:
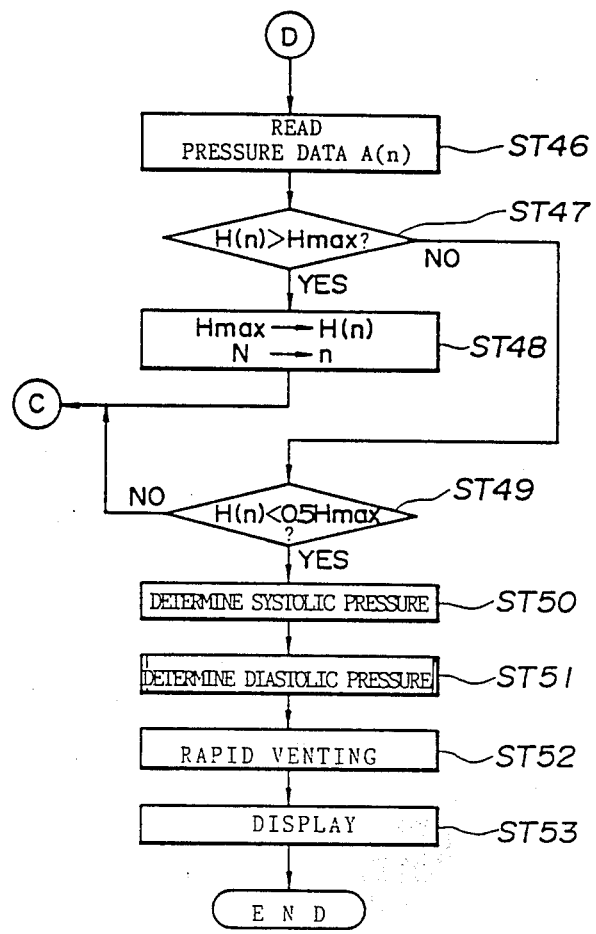
Figure 11:
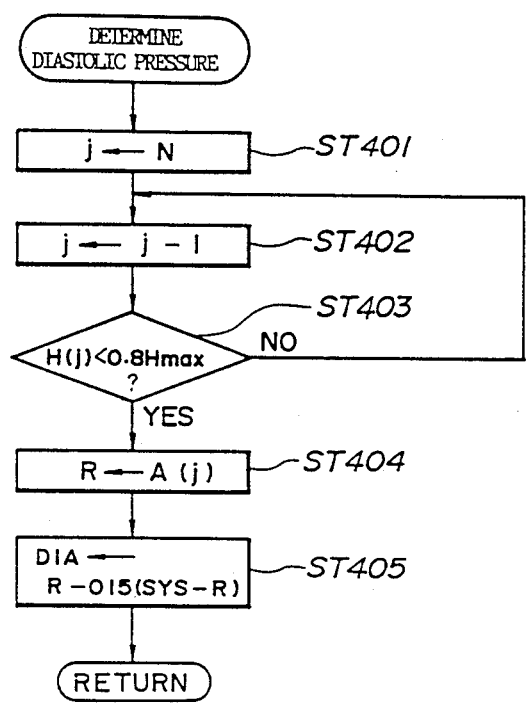
FIG. 11 is a flow chart showing an essential part of the processing action for determining the systolic pressure in accordance with the fourth embodiment of the present invention.

FIGS. 10a and 10b constitute a flow chart showing the action of determining the blood pressures according to a fourth embodiment of the present invention (which was described with reference to FIG. 12), and FIG. 11 is a flow chart of the subroutine in ST51 for determining the diastolic pressure which characterizes the present embodiment.

A main feature of the present embodiment exists in that the blood pressure values are obtained during the course of increasing the cuff pressure. Therefore, as far as the process of ST31 through ST50 is concerned, there is no special feature and nothing is different from the previous embodiment except for the way the cuff 1 is pressurized and depressurized.

Specifically, in this embodiment, first, the cuff 1 is rapidly pressurized to a level (predetermined pressure level) which is sufficiently lower than the diastolic pressure (ST31). When the cuff 1 has been pressurized to this predetermined level, the determination result of ST32 is affirmative and the rapid pressurization is stopped (ST33).

Thereafter, the rapid pressurization process is replaced by a gradual pressurization process (ST34) and the same blood pressure determining process as in the previous embodiments is executed. In this embodiment, the cuff pressure at the time point when the pulse wave amplitude value which corresponds to 50% of the maximum pulse wave amplitude value is determined as the systolic pressure (ST49).

Then, the diastolic pressure is determined in the following way. FIG. 11 shows the action of determining the diastolic pressure in this embodiment. In ST401, the number N of the maximum pulse wave amplitude value is substituted into the variable j and the pulse wave amplitude value which corresponds to 80% of the maximum pulse wave amplitude value as shown in FIG. 12 is determined (ST402 and 403). Now, suppose that the pulse wave amplitude value corresponding to 80% of the maximum pulse wave amplitude value has been determined. Then, the determination result of ST403 is affirmative and the cuff pressure (R) at this time point is obtained.

In ST405, the diastolic pressure is determined by using this value R as a reference value in the following formula:

$$DIA = R - 0.15(SYS - R)$$

In other words, the diastolic pressure is determined by subtracting 15% of the difference between the systolic pressure (SYS) and the cuff pressure R from the cuff pressure R (ST405).

According to the present invention, the relative pulse wave amplitude value is computed from the maximum pulse wave amplitude value while the reference pressure value is determined from this relative pulse wave amplitude value and the blood pressure value is obtained from this reference pressure value in accordance with a certain mathematical formula.

According to the present invention, it is not necessary to detect the cuff pressure which corresponds to 50% of the maximum pulse wave amplitude value as opposed to the conventional methods. Therefore, since the cuff pressure is not required to be raised beyond the systolic pressure of the patient, a measurement can be completed in a short time and congestion of the artery can be avoided through reduced pressurization requirement of the artery.

Further, since the pulse wave amplitude value corresponding to 50% of the maximum pulse wave amplitude value is not required to be detected, the disadvantage of being unable to obtain the systolic pressure in the case of insufficient cuff pressurization can be eliminated and the object of the present invention can be achieved in an effective manner.

Although the present invention has been shown and described with reference to the preferred embodiment thereof, it should not be considered as limited thereby. Various possible modifications and alterations could be conceived of by one skilled in the art to any particular embodiment, without departing from the scope of the invention.

What we claim is:

1. An electronic blood pressure meter, comprising a cuff, a pressurization means for pressurizing the cuff, a pressure detection means for detecting a fluid pressure inside the cuff, a pulse wave detection means for detecting a pulse wave component contained in an output signal of the pressure detecting means, a pulse wave amplitude value computing means for computing a pulse wave amplitude value from the pulse wave component detected by the pulse wave component detecting means, and a blood pressure determining means for determining a systolic pressure and a diastolic pressure from an output signal of the pulse wave amplitude computing means, said blood pressure determining means comprising:

a relative amplitude value computing means for computing a relative pulse wave amplitude value related to and less than a maximum pulse wave amplitude value obtained by the pulse wave amplitude value computing means;

a reference pressure value computing means for computing a reference pressure value from the cuff pressure when an amplitude of the pulse wave signal has coincided with the relative amplitude value during a change in the amplitude value of the pulse wave signal, said reference pressure value being different from the systolic pressure and the diastolic pressure; and a blood pressure computing means for computing one of said systolic pressure and diastolic pressure using the reference pressure value obtained by the reference pressure value computing means in accordance with a predetermined arithmetic formula.

2. An electronic blood pressure meter as claimed in claim 1, wherein said blood pressure determining means further comprises diastolic pressure determining means for determining the diastolic pressure, and wherein said blood pressure computing means computes the systolic pressure by adding a fraction of a pressure difference between the diastolic pressure and the reference pressure value to one of the diastolic pressure and the reference pressure value.

3. An electronic blood pressure meter as claimed in claim 1, wherein said blood pressure determining means further comprises systolic pressure determining means for determining the systolic pressure, and wherein said blood pressure computing means computes the diastolic pressure by adding a fraction of a pressure difference between the systolic pressure and the reference pressure value to one of the systolic pressure and the reference pressure value.

4. An electronic blood pressure meter as claimed in claim 1, wherein a relative amplitude value computed by said relative amlitude value computing means is a pulse wave amplitude value at an arbitrary cuff pressure which is higher than a cuff pressure at which a maximum pulse wave amplitude is detected, and wherein said blood pressure computing means computes the systolic pressure using a ratio of the pulse wave amplitude value at the arbitrary cuff pressure to the maximum pulse wave amplitude.

5. An electronic blood pressure meter as claimed in claim 1, wherein a relative amplitude value computed by said relative amplitude value computing means is a pulse wave amplitude value at an arbitrary cuff pressure which is lower than a cuff pressure at which a maximum pulse wave amplitude is detected, and wherein said blood pressure computing means computes the diastolic pressure using a ratio of the pulse wave amplitude value at the arbitrary cuff pressure to the maximum pulse wave amplitude.

6. An electronic blood pressure meter, comprising a cuff, a pressurization means for pressurizing the cuff, a pressure detection means for detecting a fluid pressure inside the cuff, a pulse wave detection means for detecting a pulse wave component contained in an output signal of the pressure detecting means, a pulse wave amplitude value computing means for computing a pulse wave amplitude value from the pulse wave component detected by the pulse wave component detecting means, and a blood pressure determining means for determining a systolic pressure and a diastolic pressure from an output signal of the pulse wave amplitude computing means, said blood pressure determining means comprising:

means for determining whether the pulse wave amplitude value at an initial cuff pressure is greater than a predetermined percentage of a maximum pulse wave amplitude;

a relative amplitude value computing means for computing a relative pulse wave amplitude value related to and less than the maximum pulse wave amplitude value obtained by the pulse wave amplitude value computing means;

a reference pressure value computing means for computing a reference pressure value from the cuff pressure when an amplitude of the pulse wave signal has coincided with the relative amplitude value during a change in the amplitude value of the pulse wave signal, said reference pressure value being different from the systolic pressure and the diastolic pressure; and a blood pressure computing means for computing said systolic pressure using the reference pressure value obtained by the reference pressure value computing means in accordance with a predetermined arithmetic formula only when said determining means determines that the pulse wave amplitude value at the initial cuff pressure is greater than the predetermined percentage of the maximum pulse wave amplitude.

* * * * *